United States Patent [19]

Schumacher et al.

[11] Patent Number: 5,777,111
[45] Date of Patent: Jul. 7, 1998

[54] PROCESS FOR THE PREPARATION OF 3-(N-ARYL-AMINO)-PROPYL-2'-SULFATO-ETHYLSULFONYL COMPOUNDS

[75] Inventors: Christian Schumacher; Michael Meier, both of Frankfurt am Main; Werner Hubert Russ, Flörsheim, all of Germany

[73] Assignee: Hoechst Aktiengesellschaft, Germany

[21] Appl. No.: 862,549

[22] Filed: May 23, 1997

Related U.S. Application Data

[62] Division of Ser. No. 560,539, Nov. 17, 1995, Pat. No. 5,672,738.

[30] Foreign Application Priority Data

Nov. 18, 1994 [DE] Germany ............ 44 41 147.2

[51] Int. Cl.$^6$ .................................................. C07D 413/12
[52] U.S. Cl. .................................................. 544/97
[58] Field of Search .................................................. 544/97

[56] References Cited

U.S. PATENT DOCUMENTS

| 5,410,081 | 4/1995 | Kunde et al. ............ 564/413 |
| 5,416,234 | 5/1995 | Meier et al. ............ 558/29 |

FOREIGN PATENT DOCUMENTS 0629667  12/1994  European Pat. Off. .

OTHER PUBLICATIONS

R.J. Stoffel et al., "The preparation of 2-imidazolones. A novel ring closure of propynlureas with phosphorus pentachloride", Journal of Organic Chemistry Bd. 27. pp. 3079-3083 (1962).

J.S. Pierce et al. "Tetrahydro-1,3,2-oxazones and substituted gamma-amino propanols". Journal of the American Chemical Society. Bd. 45, pp. 790-795 (1923).

Dox, A. W., et al. "Gamma-Chloropropyl Urethans and a Synthesis of the 1,3-Oxazine Ring" *J. Am. Chem. Soc.* 45: 723-727 (1923).

Fancher, L. W., et al., "Anomalous Ring Opening of N-Aryl-2-Oxazolidinones By Anhydrous Alkoxide: A Convenient Preparation of N-(Alkoxyethyl)-2,6-Disubstituted Anilines" *Tetrahedron Letters* 29: 5095-5098 (1988).

Huang, Y., et al., "X-ray and $^1$H NMR Studies of the Conformational Equilibria of 2-Z-3-Phenyl-1,3,2-oxazaphosphorinanes. Steric and Stereoelectronic Influences on the Unexpected Axial Preferences of Me$_2$N and MeNH Substituents on Three-Coordinate Phosphorus" *J. Org. Chem.* 58: 6235-6246 (1993).

*Primary Examiner*—Joseph McKane
*Assistant Examiner*—Taofiq A. Solola
*Attorney, Agent, or Firm*—Connolly & Hutz

[57] ABSTRACT

A compound of the formula (2a)

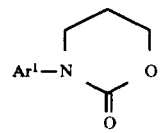

(2a)

in which

Ar$^1$ is 2-sulfophenyl, 3-sulfophenyl, 4-sulfophenyl, 2,5-disulfophenyl, 3-sulfo-4-aminophenyl, 4-sulfo-3-aminophenyl, 3-methoxy-5-sulfophenyl, 3-sulfo-4-methylphenyl, 3-sulfo-4-methoxyphenyl, 2,5-disulfo-4-methylphenyl, 2,5-disulfo-4-methoxyphenyl, 2,5-disulfo-4-aminophenyl, 5,7-disulfo-naphth-2-yl, 4,8-disulfo-naphth-2-yl, 3,6,8-trisulfo-napth-2-yl, 4,6,8-trisulfo-naphth-2-yl, 8-sulfonaphth-1-yl, 6-sulfo-naphth-1-yl or 7-sulfo-naphth-1-yl.

19 Claims, No Drawings

PROCESS FOR THE PREPARATION OF 3-(N-ARYL-AMINO)-PROPYL-2'-SULFATO-ETHYLSULFONYL COMPOUNDS

This application is a division of Ser. No. 08/560,539 which was filed on Nov. 17, 1995 now U.S. Pat. No. 5,672,738.

DESCRIPTION

Process for the preparation of 3-(N-aryl-amino)-propyl-2'-sulfatoethyl-sulfonyl compounds.

The present invention relates to the technical field of reactive dyestuff precursors. 3-(N-Aryl-amino)-propyl-2'-sulfatoethyl-sulfonyl compounds are valuable intermediate products for the preparation of reactive dyestuffs.

The present invention was based on the object of providing a process for the preparation of said intermediate products in a high yield and purity.

It has been found that the object is achieved, surprisingly, if the process steps described below are carried out.

The invention relates to a process for the preparation of compounds of the formula (1)

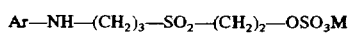

$$Ar-NH-(CH_2)_3-SO_2-(CH_2)_2-OSO_3M \quad (1)$$

in which
M is an alkali metal or hydrogen and
Ar is an aromatic radical of the formula

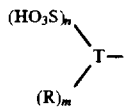

in which
n is a number from 0 to 3,
m is a number from 0 to 3,
R is $C_1$–$C_4$-alkyl, $C_1$–$C_4$-alkoxy, amino, $C_1$–$C_4$-alkylamino, di-($C_1$–$C_4$)-alkylamino, $C_6$–$C_{10}$-arylamino, $C_1$–$C_4$-acylamino, ureido, nitro or cyano, where $C_1$–$C_4$-alkyl and $C_6$–$C_{10}$-aryl can be substituted by one to three radicals from the group consisting of $C_1$–$C_4$-alkoxy, halogen, hydroxy, carboxy, sulfo, sulfato, nitro, cyano and a combination thereof,
and
T is an aromatic bridge member from the benzene or naphthalene series,
which comprises reacting a compound of the formula (2)

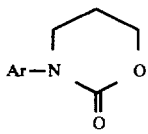

with 2-mercaptoethanol to give a compound of the formula (3)

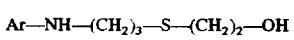

$$Ar-NH-(CH_2)_3-S-(CH_2)_2-OH \quad (3)$$

at temperatures from 90° to 270° C. in the presence of a catalytic amount of a base, oxidizing the compound of the formula (3) to give a compound of the formula (4)

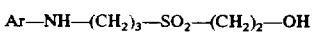

$$Ar-NH-(CH_2)_3-SO_2-(CH_2)_2-OH \quad (4),$$

and esterifying the compound of the formula (4) with at least one molar equivalent of sulfuric acid, oleum or halosulfonic acid to give a compound of the formula (1).

Compounds which are preferred in the context of the present invention are those of the formula (1) in which
M is hydrogen, sodium or potassium,
n is the number 0 or 1,
m is the number 0 or 1, preferably 0,
R is methyl, ethyl, methoxy, ethoxy, methylamino or, in particular, amino and
Ar is phenyl, 2-sulfophenyl, 3-sulfophenyl, 4-sulfophenyl, 2,5-disulfophenyl, 2-methylphenyl, 3-methylphenyl, 4-methylphenyl, 2-methoxyphenyl, 3-methoxyphenyl, 4-methoxyphenyl, 3-aminophenyl, 4-aminophenyl, 3-sulfo-4-aminophenyl, 4-sulfo-3-aminophenyl, 3-methoxy-5-sulfophenyl, 3-sulfo-4-methylphenyl, 3-sulfo-4-methoxyphenyl, 2-sulfo-4-methylphenyl, 4-methyl-2-sulfophenyl, 2-sulfo-4-methoxyphenyl, 2,5-disulfo-4-methylphenyl, 2,5-disulfo-4-methoxyphenyl, 2,5-disulfo-4-aminophenyl, 5,7-disulfo-naphth-2-yl, 4,8-disulfo-naphth-2-yl, 3,6,8-trisulfo-naphth-2-yl, 4,6,8-trisulfo-naphth-2-yl, 8-sulfo-naphth-1-yl, 6-sulfo-naphth-1-yl or 7-sulfo-naphth-1-yl.

Examples of particularly preferred 3-(N-aryl-amino)-propyl-2'-sulfatoethyl-sulfonyl compounds of the formula (1) are the following compounds (1a), (1b) and (1c)

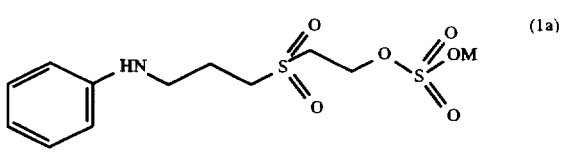

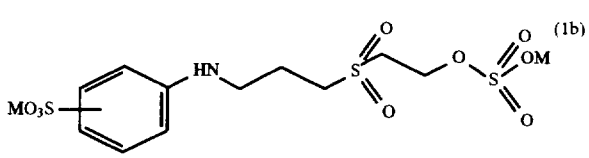

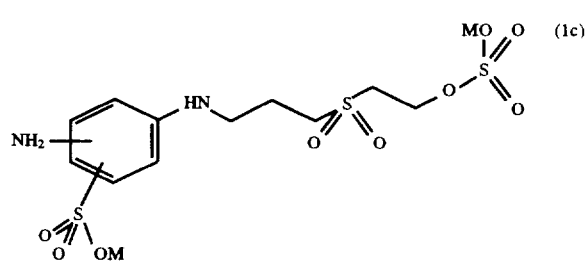

in which M is hydrogen or an alkali metal, preferably Na.

The process according to the invention starts from a 3-aryl-2H-1,3-oxazin-2-one of the formula (2), which is reacted with 1 to 3 times the molar amounts of mercaptoethanol in the presence of a catalytic amount of a base, such as an alkali metal hydroxide, carbonate, phosphate or alcoholate or alkaline earth metal hydroxide, carbonate, phosphate or alcoholate, preferably sodium carbonate, potassium carbonate, cesium carbonate, sodium hydroxide, potassium hydroxide or sodium methanolate, in bulk or in one of the solvents mentioned below or in a solvent-water mixture, preferably in bulk or in an aliphatic hydrocarbon, at a temperature of 90° to 270° C., preferably 160° to 240° C., preferably in an inert gas atmosphere and if appropriate under reduced pressure, with ring opening and splitting off of $CO_2$ to give novel 3-(N-arylamino)-propyl-2'-hydroxyethyl sulfide compounds of the formula (3).

A catalytic amount is understood as meaning concentrations of 1 to 15 mol %, based on the compound of the formula (2).

Suitable solvents are, for example, alcohols, ethers or amides, such as ethanol, propanol, isopropanol, dimethoxyethane, diethylene glycol dimethyl ether, dimethylacetamide, N-methylpyrrolidone and/or aliphatic hydrocarbons, such as decane or undecane.

Ring openings of cyclic urethanes with $CO_2$ being split off are already known in principle, for example the ring opening of cyclic 5-membered ring urethanes by alcoholate to give 2-alkoxyethyl-aniline derivatives in Tetrahedron Letters 29 (1988), 5095 or the hydrolysis of 3-phenyl-tetrahydro-2H-1,3-oxazin-2-one to give 3-hydroxypropyl-aniline in C. R. Hebd. Seances Acad. Sci. Ser. C. (1975), 280(20), 1269. Such compounds of the formula (2) in which Ar is phenyl or o-methylphenyl are known from J. Am. Chem. Soc. 45 (1923), 723.

Compounds of the formula (2a)

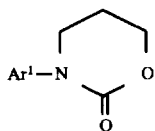 (2a)

in which
$Ar^1$ is 2-sulfophenyl, 3-sulfophenyl, 4-sulfophenyl, 2,5-disulfophenyl, 3-sulfo-4-aminophenyl, 4-sulfo-3-aminophenyl, 3-methoxy-5-sulfophenyl, 3-sulfo-4-methylphenyl, 3-sulfo-4-methoxyphenyl, 2-sulfo-4-methylphenyl, 2,5-disulfo-4-methylphenyl, 2,5-disulfo-4-methoxyphenyl, 2,5-disulfo-4-aminophenyl, 5,7-disulfo-naphth-2-yl, 4,8-disulfo-naphth-2-yl, 3,6,8-trisulfo-naphth-2-yl, 4,6,8-trisulfo-naphth-2-yl, 8-sulfo-naphth-1-yl, 6-sulfo-naphth-1-yl or 7-sulfonaphth-1-yl and
M is an alkali metal or hydrogen,
are novel and the present invention relates to them.

The present invention also relates to the process described below for the preparation of cyclic urethanes of the formulae (2) and (2a), which has advantages in respect of yield and profitability in comparison to the process described in J. Am. Chem. Soc. 45 (1923), 723.

Cyclic urethanes of the formula (2) are prepared by reacting an open-chain compound of the formula (8)

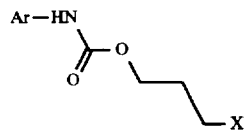 (8)

in which
Ar has the meaning defined above and
X is a leaving group from the group consisting of halogen, such as chlorine, bromine or iodine, sulfato, $C_1$–$C_4$-alkoxy, such as methoxy or ethoxy, $C_1$–$C_4$-alkylcarbonyloxy, such as acetyloxy, ($C_6$–$C_{10}$-aryl)carbonyloxy, $C_1$–$C_4$-alkylsulfonyloxy, ($C_6$–$C_{10}$-aryl)sulfonyloxy and a radical $NR^1R^2R^3$, in which the radicals $R^1$, $R^2$ and $R^3$ are $C_1$–$C_4$-alkyl, such as methyl or ethyl, $C_6$–$C_{10}$-aryl-$C_1$–$C_4$-alkylene, such as benzyl, or $C_6$–$C_{10}$-aryl, such as phenyl, $C_1$–$C_4$-alkyl or $C_6$–$C_{10}$-aryl-$C_1$–$C_4$-alkylene being preferred, with the proviso that at least two of the radicals $R^1$, $R^2$ and $R^3$ are $C_1$–$C_4$-alkyl, X preferably here being the radicals chlorine, bromine, sulfato, methoxy, ethoxy, acetyloxy, dimethylbenzylammonium, trimethylammonium, and particularly preferably chlorine; with elimination of HX, by the action of 0.8 to 1.2 molar equivalents of a base at a pH of 10 to 13, preferably 11 to 12, at temperatures from 25° to 100° C., preferably 50° to 80° C., to give a cyclic urethane of the formula (2). Cyclic urethanes of the formula (2a) are prepared in the same manner.

The reaction can be carried out in water, one of the abovementioned solvents or in a solvent-water mixture.

Examples of suitable bases are alkali metal or alkaline earth metal hydroxides, phosphates, silicates, alcoholates or carbonates, alkali metal alcoholates and hydroxides being preferred. The preferred process variant according to the invention furthermore comprises metering in the base slowly, i.e. over a period of 1 to 4 hours. In the case where the radical Ar carries no sulfo group (n=0), the reaction is preferably carried out in an alcohol, such as isopropanol or ethanol. In the case where Ar carries 1 to 3 sulfo groups (n=1 to 3), the reaction is preferably carried out in water.

The compounds of the formula (2) thus prepared can be purified by crystallization at temperatures below 20° C., for example from ethanol at a temperature of –20° to 5° C. in the case where Ar is phenyl or sulfophenyl.

Compounds of the formula (8) can be prepared from an amine of the formula

 Ar—$NH_2$ and a compound of the formula (9)

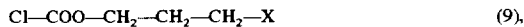 Cl—COO—$CH_2$—$CH_2$—$CH_2$—X (9), in which Ar and X have one of the abovementioned meanings, in water or a solvent in the presence of a base. The compound of the formula (9) is, for example, 3-chloropropyl chloroformate. This procedure has already been described in principle in J. Am. Chem. Soc. 45, 723 (1923). The process according to the invention comprises initially introducing the amine into the reaction vessel in water, in a solvent or in a solvent-water mixture and slowly metering in the compound of the formula (9) and the base simultaneously, with pH control, by which means better yields and a higher purity than in the known procedure mentioned are achieved. In the case where Ar carries 1 to 3 sulfo groups, the process according to the invention comprises carrying out the reaction in water at 10° to 30° C. at a pH of 6 to 8, and in the case where Ar is free from sulfo groups, it comprises carrying out the reaction in a solvent or in a water-solvent mixture at 10° to 30° C. and at a pH of 6 to 8. Possible bases and solvents are those already described above.

An alternative process variant for the preparation of a compound of the formula (8) comprises reacting an isocyanate of the formula

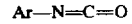 Ar—N=C=O and a compound of the formula (10)

 HO—$CH_2$—$CH_2$—$CH_2$—X (10), in which Ar and X have one of the abovementioned meanings, with one another to give a compound of the formula (8). The compound of the formula (10) is, for example, 3-chloropropanol, 3-bromopropanol, 3-(alkylcarbonyloxy)-propanol or 3-sulfato-propanol. This procedure has already been described in principle in J. Am. Chem. Soc. 45, 723 (1923). There, the reaction is carried out at 150° C. (X=Cl), which is adverse for the yields and product qualities. The reaction in general proceeds better at temperatures from 10° to 120° C., preferably 20° to 90° C., and in the case where X is chlorine, preferably at 55° to 80° C., in bulk or in a solvent which is inert with respect to the reaction conditions, such as, for example, toluene.

The process using the isocyanate of the formula Ar—N=C=O is preferred for radicals Ar which are free from sulfo groups.

The process using the amine of the formula Ar—NH$_2$ is preferred for radicals Ar which carry 1 to 3 sulfo groups.

Another process variant according to the invention for the preparation of compounds of the formula (2), preferably for compounds in which Ar is free from sulfo groups, comprises reacting an N-aryl-3-hydroxypropylamine compound of the formula (11)

the preparation of which is described, for example, in J. Org. Chem. 58 (1993), 6235 for Ar as phenyl, with a compound of the formula $$X^1-CO-X^2 \qquad (12)$$

in which

X$^1$ is halogen, preferably chlorine, or C$_1$–C$_4$-alkoxy, preferably methoxy or ethoxy, and X$^2$ independently of X$^1$ has one of the meanings of X$^1$.

Examples of preferred compounds of the formula (12) are phosgene, methyl chlorocarbonate, ethyl chlorocarbonate, dimethyl carbonate or diethyl carbonate. According to the invention, the compounds of the formula (2) are prepared from the compounds of the formula (11) and (12) mentioned, at temperatures of from 80° to 140° C. in the case where one or both of the radicals X$^1$ or X$^2$ is C$_1$–C$_4$-alkoxy, or at 20° to 140° C. in the case where X$^1$ and X$^2$ are both halogen, in the presence of a base.

The base in the case where X$^1$ and X$^2$ are C$_1$–C$_4$—alkoxy is a catalytic amount of base or in the case where one of the radicals X$^1$ or X$^2$ is halogen is a molar amount of a base or in the case where both radicals X$^1$ and X$^2$ are halogen is twice the molar amount of the base. Bases which are of particular interest are alkali metal alcoholates, for example sodium methanolate.

The intermediate compounds of the formula (3) prepared by reaction of a cyclic urethane of the formula (2) with 2-mercaptoethanol were not previously known and the present invention relates to them. Preferred compounds of the formula (3) are those in which Ar is phenyl, 2-sulfophenyl, 3-sulfophenyl, 4-sulfophenyl, 2,5-disulfophenyl, 2-methylphenyl, 3-methylphenyl, 4-methylphenyl, 2-methoxyphenyl, 3-methoxyphenyl, 4-methoxyphenyl, 3-aminophenyl, 4-aminophenyl, 3-sulfo-4-aminophenyl, 4-sulfo-3-aminophenyl, 3-methoxy-5-sulfophenyl, 3-sulfo-4-methylphenyl, 3-sulfo-4-methoxyphenyl, 2-sulfo-4-methylphenyl, 4-methyl-2-sulfophenyl, 2-sulfo-4-methoxyphenyl, 2,5-disulfo-4-methylphenyl, 3,5-disulfo-4-methoxyphenyl, 2,5-disulfo-4-aminophenyl, 5,7-disulfo-disulfo-naphth-2-yl, 3,6,8-trisulfo-naphth-2-yl, 4,6,8-trisulfo-naphth-2-yl, 8-sulfo-naphth-1-yl, 6-sulfo-naphth-1-yl or 7-sulfo-naphth-1-yl and M is hydrogen or an alkali metal.

The invention also relates to a process for the preparation of a compound of the formula (1), which comprises reacting a compound of the formula (3) at temperatures from 90° to 270° C. in the presence of a catalytic amount of a base, oxidizing the compound of the formula (3) to give a compound of the formula (4)

and esterifying the compound of the formula (4) with at least one molar equivalent of sulfuric acid, oleum or halosulfonic acid to give a compound of the formula (1).

The compound of the formula (3) is oxidized in bulk or expediently in an organic solvent which is inert with respect to the reaction conditions, for example N-methylpyrrolidone or dimethylacetamide, to give the compound of the formula (4), preferably using hydrogen peroxide as the oxidizing agent and in the presence of a preferably catalytic amount of a transition metal-oxygen compound, such as sodium tungstate, tungsten oxide or sodium vanadate, at a temperature of between 70° and 110° C. Catalytic amount is understood here as meaning 0.2 to 5, preferably 0.5 to 2, parts by weight of the transition metal compound mentioned per mole of thioether of the formula (3). The amount of hydrogen peroxide is expediently 1.8 to 2.2 molar equivalents, based on the compound of the formula (3) to be oxidized.

The compounds of the formula (4) are esterified with 1 to 1.5 molar equivalents, preferably 1.05 to 1.2 molar equivalents, of sulfuric acid, optionally comprising contents of SO$_3$, or with 1 to 1.5, preferably 1.05 to 1.2, molar equivalents of a halosulfonic acid, preferably chlorosulfonic acid, to give sulfatoethylsulfone compounds of the formula (1) (M=hydrogen).

It is expedient to free the reaction mixture from water by the action of heat and/or reduced pressure before the esterification and to carry out the esterification in said inert organic solvent at temperatures of between 0° and 40° C., preferably 10° and 30° C., without intermediate isolation of the sulfone of the formula (4).

The compound of the formula (1) is then isolated as the sulfonic acid (M=H) or as the alkali metal salt (M=Li, Na or K), isolation as the alkali metal salt, in particular as the sodium salt, being preferred. For this, said solvent is removed by distillation, preferably under reduced pressure.

In an alternative embodiment, the 3-(N-arylamino)-propyl-2'-hydroxyethyl sulfide compound of the formula (3) is reacted in water with an anhydride or acid chloride, for example with acetyl chloride, trifluoroacetyl chloride, acetic anhydride or trifluoroacetic anhydride, to give a 3-(N-arylacyl-amino)-propyl-2'-hydroxyethyl sulfide compound of the formula (7)

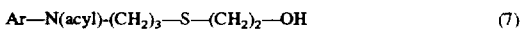

in which acyl is an optionally substituted C$_1$–C$_4$-alkyl-carbonyl radical, preferably acetyl, trichloroacetyl or trifluoroacetyl.

The oxidation of the compound of the formula (7) to give the sulfonyl compound is carried out as already described, but comprises a procedure which can also be carried out in water, as well as in bulk or in the organic solvents mentioned, water being the preferred solvent.

The acyl group is split off hydrolytically from the resulting sulfonyl compound in the alkaline or acid range, preferably in an acid, hydrochloric acid or sulfuric acid, aqueous solution, such as, for example, in 5 to 30% strength by weight aqueous hydrochloric acid or sulfuric acid in the case where acyl is acetyl, at a temperature of between 80° and 100° C., the compound of the formula (4) being obtained in aqueous solution.

The compounds of the formula (1) prepared by the process according to the invention are distinguished by a yield of 70 to 80% (only organic contents, the product isolated also comprises inorganic salts) and a purity of 80 to 90%, calculated over all the synthesis stages, and are used, in particular, for the preparation of reactive dyestuffs for dyeing fibrous materials (EP-A-O 629 667).

In the following examples, "parts" are parts by weight.
Example 1 Ar=phenyl
Stage 1

119 parts of phenyl isocyanate are metered into 120 parts of 3-chloropropanol, which have been initially introduced into the reaction vessel. at 60° C. in the course of 2 hours. The reaction is then continued at this temperature, while stirring, for a further period of time to give chloropropylphenylurethane of the formula

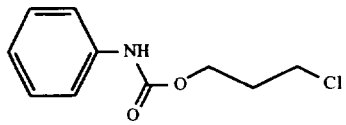

as an oil which crystallizes when cooled in an ice bath. The reaction is virtually quantitative.

$^1$H—NMR (d$_6$DMSO):
2.09 2H. qi; 3.74 2H. t; 4.21 2H. t;
6.96–7.02 1H. m; 7.24–7.32 2H. m; 7.46–7.52 2H. m

Stage 2 a) Variant 1

500 ml of isopropanol are added to the oil from stage 1. 120 parts of a 33% strength by weight sodium hydroxide solution are then metered in at a temperature of 70° C. in the course of 2 hours. The solvent is subsequently removed under reduced pressure and the product is crystallized from ethanol at a temperature of −5° to +5° C. The crystals are dried under reduced pressure at 60° C. to give 150 parts of N-phenyltetrahydro-oxazinon-2-one of the formula

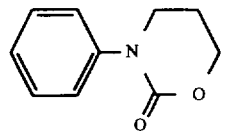

$^1$H—NMR (d$_6$- DMSO):
2.09 2H. m; 3.65 2H. t; 4.33 2H. t;
7.21–7.27 1H. m; 7.32–7.42 4H. m;

b) Variant 2

213.7 parts of chloropropylphenylurethane from stage 1 are initially introduced into the reaction vessel with 1000 parts of 2-propanol, and 50 parts of sodium hydroxide are metered in at 50° C. in the course of 2 hours. The mixture is then heated to 85° C. and subsequently stirred at this temperature for 4 hours. The suspension is filtered and the filter cake is washed with 200 parts of isopropanol. The filtrate is evaporated to dryness. 173.9 parts of N-phenyltetrahydro-oxazinon-2-one are obtained with a purity of 88%. This corresponds to a yield of 86% of theory.

c) Variant 3

428 parts of chloropropylphenylurethane from stage 1 are initially introduced into the reaction vessel with 428 parts of dimethoxyethane. 85 parts of sodium hydroxide are metered in at 50° C. in the course of 4 hours and the mixture is heated to 80° C. in the course of 3 hours. It is then subsequently stirred at this temperature for 4 hours. The suspension is filtered at 70° C. and the filter cake is washed with 214 parts of dimethoxyethane. The filtrate is evaporated to dryness. The residue is treated with 214 parts of dimethoxyethane at 0°C. 306.6 parts of N-phenyltetrahydro-oxazin-2-one are obtained with a purity of >99%. This corresponds to a yield of 86% of theory. A further 20 parts of product can be obtained from the mother liquor.

Stage 3 a) Variant 1

12 parts of a 33% strength by weight sodium hydroxide solution are added to 95 parts of 2-mercaptoethanol under a nitrogen atmosphere. 177 parts of the compound from stage 2 are then sprinkled in as the solid. The reaction is brought to completion at 150° C. under a nitrogen atmosphere. Volatile substances in the reaction mixture are then distilled off under reduced pressure. 210 parts of 3-(N-phenylamino)-propyl-2'-hydroxyethyl sulfide of the formula

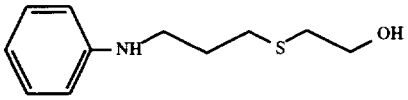

are obtained with a purity of 80% as a yellow oil; this corresponds to a yield of 80% of theory.

$^1$H—NMR (D$_6$- DMSO):
1.76 2H. qi; 2.59 2H. t; 2.60 2H. t; 3.09 2H. t;
3.58 2H. t; 5.00 2H. s; 6.54–6.67 2H. m; 6.90–7.22 2H. m.

b) Variant 2

0.5 part of potassium carbonate and 86 parts of 2-mercaptoethanol are added to 177 parts of N-phenyltetrahydro-oxazin-2-one and the mixture is heated to 225° C. under a nitrogen atmosphere. It is subsequently stirred at this temperature for 1.5 hours. 215 parts of 3-(N-phenylamino)-propyl-2'-hydroxyethyl sulfide are obtained with a purity of 84%; this corresponds to a yield of 86%.

c) Variant 3

1.0 part of cesium carbonate and 82 parts of 2-mercaptoethanol are added to 177 parts of N-phenyltetrahydro-oxazin-2-one and the mixture is heated to 190° C. under a nitrogen atmosphere. It is subsequently stirred at this temperature for 6 hours. 208 parts of 3-(N-phenylamino)-propyl-2'-hydroxyethyl sulfide are obtained with a purity of 85%; this corresponds to a yield of 83%.

d) Variant 4

0.5 part of potassium carbonate, 86 parts of 2-mercaptoethanol and 40 parts of decane are added to 177 parts of N-phenyltetrahydro-oxazino-2-one and the mixture is heated to 169° C. under a nitrogen atmosphere. It is stirred at this temperature for 6 hours. The solvent is then distilled off in vacuo. 216 parts of 3-(N-phenyl-amino)-propyl-2'-hydroxyethyl sulfide are obtained with a purity of 87%; this corresponds to a yield of 89%.

Stage 4

1000 parts of anhydrous dimethylacetamide and 1 part of sodium tungstate are added to 210 parts of 3-(N-phenyl-amino)-propyl-2'-hydroxyethyl sulfide at 25° C. 194 parts of a 35% strength by weight aqueous solution of hydrogen peroxide are then added at a temperature of 80° to 90° C. in the course of 4 hours. The mixture is subsequently stirred at this temperature for a further hour to give 242 parts of the compound of the formula

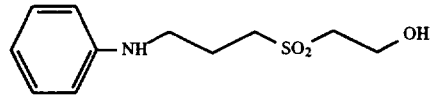

as a solution in dimethylacetamide. The conversion is virtually quantitative.

Stage 5

Variant 1:

The solution comprising dimethylacetamide from stage 4 is then substantially freed from water in vacuo. 125 parts of chlorosulfonic acid are slowly added to the bottom product which remains at 10° to 25° C., while cooling with ice. The mixture is subsequently stirred for a further period of time and neutralized to pH 4 to 5 while sprinkling in solid sodium carbonate, the inorganic constituents are filtered off and the volatile constituents are substantially distilled off at a bottom temperature of up to 60° C. under reduced pressure to give 335 parts of the compound of the formula

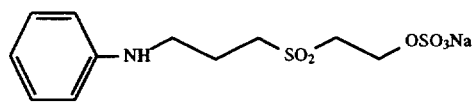

as an approximately 40% strength solution in dimethylacetamide, which is used for further syntheses, for example for the preparation of dyestuffs, without further isolation.

$^1$H—NMR analyses (100 MHz) in $d_6$-dimethyl sulfoxide against $Si(CH_3)_4$ as the standard:
1.71–2.03 ppm (m,2H), 2.94–3.24 ppm (dt,2H),
3.25–3.50 ppm (t,2H;t,2H), 4.07 ppm (t,2H)
5.61 ppm (broad, 1H), 6.40–6.63 ppm (m,3H),
6.87–7.14 ppm (m,2H).

Variant 2:

The process according to stage 4 is carried out with N-methylpyrrolidone instead of dimethylacetamide as the solvent and using 119 parts of chlorosulfonic acid. 335 parts of the compound mentioned in Variant 1 are obtained.

Example 2 Ar=3-sulfophenyl
Stage 1 and 2 combined:

173 parts of 3-sulfoaniline are dissolved in 500 parts of water at a pH of 7. 165 parts of 3-chloropropyl chloroformate are added dropwise at 20° to 25° C. in the course of 2 hours, the pH being kept at 6 to 7 with 10% strength sodium carbonate solution. The mixture is subsequently stirred for a further period of time and the pH is then increased to 11.5 to 12. The reaction is brought to completion at this pH at a temperature of 70° C. The batch is evaporated in vacuo and the residue is crystallized from ethanol to give the compound of the formula

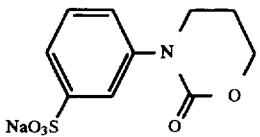

$^1$H—NMR ($d_6$- DMSO)
2.09 2H, m; 3.64 2H, t; 4.34 2H, t;
7.26–7.31 1H, m; 7.46–7.51 1H, m; 7.56–7.58 1H, m
7.34 1H, t.

Stage 3

8 parts of sodium methylate are added to 90 parts of mercaptoethanol in an inert gas atmosphere. The mixture is heated to 80° C., methanol is driven off in a stream of gas and 313 parts of the compound from the preceding stage 1 and 2 are then sprinkled in. The mixture is then heated to 140° to 150° C. It is subsequently stirred for a further period of time, until the reaction has ended. A compound of the formula

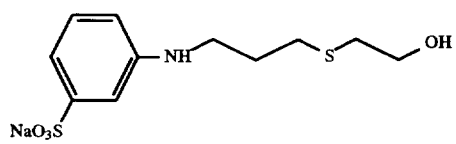

is isolated by stirring the resulting oil in ethanol, the product being obtained as a white solid. It is filtered off, washed with ethanol and dried in vacuo.

$^1$H—NMR ($d_6$- DMSO):
1.77 2H, qi; 2.57 2H, t; 2.60 2H, t; 3.07 2H, q
3.52 2H, q; 4.80 1H, t; 5.67 1H, t; 6.48 1H, m;
6.76–6.80 1H, dd; 6.85–6.88 1H, m; 7.00 1H, t;

Stage 4 and 5 combined:

238 parts of the compound from stage 3 are introduced into 1000 parts of dimethylacetamide and are dissolved, while stirring, and 1 part of $NaVO_3$ is added. 130 parts of hydrogen peroxide as an approximately 40% strength by weight solution in dimethylacetamide are then added at a temperature of 80° to 90° C. and the mixture is subsequently stirred until the reaction has ended. The water present is distilled off in vacuo. 116 parts of chlorosulfonic acid are then slowly added dropwise at a temperature of 10° to 20° C. Isolation is carried out as described in Example 1 to give the compound of the formula

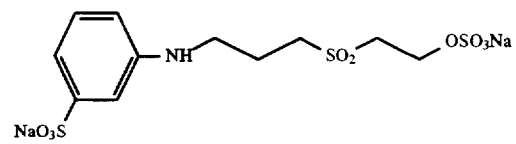

$^1$H—NMR ($d_6$- DMSO)
1.96 2H, m; 3.11 2H, t, 3.22 2H, t;
3.42 2H, t; 4.11 2H, t
6.50–6.56 1H, dd; 6.80–6.84 1H, d; 6.86–6.89 1H, m;
7.02 1H, t

Example 3 Ar=4=sulfo-phenyl
Stage 1 and 2 combined:

173 parts of 4-sulfoaniline are dissolved in 500 parts of water at a pH of 7. 165 parts of 3-chloropropyl chloroformate are added dropwise at 20° to 25° C. in the course of 2 hours, the pH being kept at 6 to 7 with 10% strength sodium carbonate solution. The mixture is subsequently stirred for a further period of time and the pH is then increased to 11.5 to 12. The reaction is brought to completion at this pH at a temperature of 70° C. The batch is evaporated in vacuo to give the compound of the formula

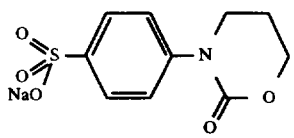

$^1$H—NMR ($d_6$- DMSO):
2.09 2H, m; 3.65 2H, t; 4.34 2H, t;
7.27–7.34 2H, m; 7.57–7.63 2H, m.

Stage 3

2 parts of potassium carbonate are added to 90 parts of mercaptoethanol in an inert gas atmosphere. 313 parts of the compound from the preceding stage 1 and 2 are then sprinkled in and the mixture is then heated to 190° to 200° C. It is subsequently stirred for a further period of time until the reaction has ended. A compound of the formula

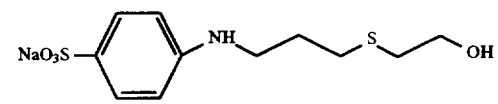

is obtained by stirring the resulting oil in ethanol, the product precipitating as a white solid. It is filtered off, washed with ethanol and dried in vacuo.

$^1$H—NMR ($d_6$- DMSO):
1.74 2H, qi; 2.54 2H, t; 2.57 2H, t; 3.06 2H, q;
3.50 2H, t; 5.83 1H, t;
6.45 2H, d; 7.32 2H, d;

Stage 4 and 5 combined:

238 parts of the compound from stage 3 are introduced into 500 parts of dimethylacetamide and are dissolved, while stirring, and 1 part of $Na_2WO_4$ is added. 130 parts of hydrogen peroxide (35% strength by weight of aqueous solution) are then added in portions at a temperature of 80° to 90° C. and the mixture is subsequently stirred until the reaction has ended. The water present is distilled off in vacuo. 116 parts of chlorosulfonic acid are then slowly added dropwise at a temperature of 10° to 20° C. The compound of the formula $$NaO_3S-\text{Ar}-NH-CH_2CH_2CH_2-SO_2-CH_2CH_2-OSO_3Na$$

is obtained and is isolated as described in Example 1.
Example 4 Ar=5-amino-4-sulfo-phenyl
Stage 1+2 combined:

165 parts of 3-chloropropyl chloroformate are added dropwise to 188 parts of the sodium salt of 2,4-diaminobenzenesulfonic acid in 1000 parts of water at a pH of 7 at 20°–25° C. in the course of 2 to 3 hours, the pH being kept at 6–7 with 10% strength by weight sodium carbonate solution. The mixture is subsequently stirred for a further period of time until the reaction has ended and the pH is then increased to 11.5 to 12. The cyclization is brought to completion at this pH at a temperature of 70° C. The batch is evaporated in vacuo to give the compound of the formula $$NaO_3S-\text{Ar}(H_2N)-N(\text{cycle})-C(=O)-O$$

as a white solid.
$^1$HMR ($d_6$- DMSO):
2.06 2H, m; 3.56 2H, t;
4.29 2H, t; 3.36 2H, s;
6.40 1H, dd; 6.56 1H, d 7.40 1H, d.
Stage 3

0.1 part of potassium carbonate is added to 240 parts of mercaptoethanol in an inert gas atmosphere. 294 parts of the compound from stage 1+2 are then sprinkled in and the mixture is then heated to 160°–170° C. The reaction is brought to completion in the course of 2 to 3 hours. A novel thioether compound of the formula $$NaO_3S-\text{Ar}(H_2N)-NH-CH_2CH_2CH_2-S-CH_2CH_2-OH$$

is obtained and is isolated by stirring the resulting oil into ethanol, the product precipitating as a white solid. It is filtered off, washed with several portions of ethanol and dried in vacuo.
$^1$HMR ($d_6$- DMSO)
1.74 2H, qi 2.57 2H, t 2.59 2H, t
3.01 2H, q 3.52 2H, m 4.79 1H, t
5.33 2H, s 5.70–5.77 2H, m 7.13 1H, d
Stage 4+5 combined:

328 parts of the compound from stage 3 are introduced into 1000 parts of water and are dissolved, while stirring, and 125 parts of acetic anhydride are added. Acylation is carried out at a pH of 3–4 and a temperature of 70°–80° C. in the course of 1 hour.

1 part of sodium tungstate is then added. 130 parts of hydrogen peroxide are then added in portions at a temperature of 80°–90° C. and the mixture is subsequently stirred until the reaction has ended. This gives the compound of the formula $$NaO_3S-\text{Ar}(H_2N)-N(COCH_3)-CH_2CH_2CH_2-SO_2-CH_2CH_2-OH$$

as a mixture with the corresponding compound acylated on N and O. It is not isolated but is further worked on directly.

For this, 150 parts of concentrated sulfuric acid are added and the batch is heated at 90°–100° C. in an inert gas atmosphere for 4 hours, the acetyl protective group being split off again hydrolytically.

After cooling to 40°–50° C., the water present and acetic acid formed are distilled off in vacuo until no further volatile constituents pass over. 500 parts of N-methyl-pyrrolidone are added to the bottom product and 130 parts of chlorosulfonic acid are slowly added dropwise to the reaction solution at a temperature of 10°–20° C. The mixture is then subsequently stirred for a further period of time and neutralized by sprinkling in solid sodium carbonate. The compound of the formula $$NaO_3S-\text{Ar}(H_2N)-NH-CH_2CH_2CH_2-SO_2-CH_2CH_2-OSO_3Na$$

is obtained as the sodium salt and is isolated as an approximately 30% strength solution in N-methylpyrrolidone as described in Example 1.

Further valuable compounds of the formula (1) are obtained if amines of the formula Ar—$NH_2$, in which the radical Ar has the meanings given in the table, are employed in stage 1 instead of the amines mentioned in Examples 1 to 4.

| 5000 hp design air core | 5000 hp design iron rotor |
| --- | --- |
| ampere turns 422,000 a | 230,000 a |
|  | (all other terms the same) |
| rotor: |  |
| inner radius 7.2 in |  |
| outer radius 8.2 in |  |
| pole angle 14 degrees |  |
| straight 30 inches poles 4 |  |
| stator: |  |
| slots 72 |  |
| inner radius 10.5 in. |  |
| phases 3 |  |
| backiron: |  |
| inner radius 13.6 |  |

We claim:
1. A compound of the formula (2a)

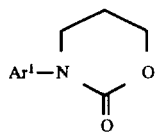 (2a)

in which
Ar¹ is 2-sulfophenyl, 3-sulfophenyl, 4-sulfophenyl, 2,5-disulfophenyl, 3-sulfo-4-aminophenyl, 4-sulfo-3-aminophenyl, 3-methoxy-5-sulfophenyl, 3-sulfo-4-methylphenyl, 3-sulfo-4-methoxyphenyl, 2,5-disulfo-4-methylphenyl, 2,5-disulfo-4-methoxyphenyl, 2,5-disulfo-4-aminophenyl, 5,7-disulfo-naphth-2-yl, 4,8-disulfo-naphth-2-yl, 3,6,8-trisulfo-napth-2-yl, 4,6,8-trisulfo-naphth-2-yl, 8-sulfonaphth-1-yl, 6-sulfo-naphth-1-yl or 7-sulfo-naphth-1-yl.

2. The compound as claimed in claim 1, wherein Ar¹ is 2-sulfophenyl.

3. The compound as claimed in claim 1, wherein Ar¹ is 3-sulfophenyl.

4. The compound as claimed in claim 1, wherein Ar¹ is 4-sulfophenyl.

5. The compound as claimed in claim 1, wherein Ar¹ is 2,5-disulfophenyl.

6. The compound as claimed in claim 1, wherein Ar¹ is 3-sulfo-4-aminophenyl.

7. The compound as claimed in claim 1, wherein Ar¹ is 4-sulfo-3-aminophenyl.

8. The compound as claimed in claim 1, wherein Ar¹ is 3-methoxy-5-sulfophenyl.

9. The compound as claimed in claim 1, wherein Ar¹ is 3-sulfo-4-methylphenyl.

10. The compound as claimed in claim 1, wherein Ar¹ is 3-sulfo-4-methoxyphenyl.

11. The compound as claimed in claim 1, wherein Ar¹ is 2,5-disulfo-4-methylphenyl.

12. The compound as claimed in claim 1, wherein Ar¹ is 2,5-disulfo-4-methoxyphenyl.

13. The compound as claimed in claim 1, wherein Ar¹ is 2,5-disulfo-4-aminophenyl.

14. The compound as claimed in claim 1, wherein Ar¹ is 5,7-disulfo-naphth-2-yl.

15. The compound as claimed in claim 1, wherein Ar¹ is 4,8-disulfo-naphth-2-yl.

16. The compound as claimed in claim 1, wherein Ar¹ is 3,6,8-trisulfo-napth-2-yl.

17. The compound as claimed in claim 1, wherein Ar¹ is 4,6,8-trisulfo-naphth-2-yl.

18. The compound as claimed in claim 1, wherein Ar¹ is 8-sulfonaphth-1-yl, or 6-sulfo-naphth-1-yl.

19. The compound as claimed in claim 1, wherein Ar¹ is 7-sulfo-naphth-1-yl.

* * * * *

UNITED STATES PATENT AND TRADEMARK OFFICE
CERTIFICATE OF CORRECTION

PATENT NO. : 5,777,111
DATED : July 7, 1998
INVENTOR(S) : Schumacher, et al

It is certified that error appears in the above-identified patent and that said Letters Patent is hereby corrected as shown below:

At column 12, lines 50-60 please delete the Table and insert the following new Table:

| Example No. | Substituent Ar |
|---|---|
| 5 | 3-methoxy-5-sulfophenyl |
| 6 | 3-methoxyphenyl |
| 7 | 3-methylphenyl |
| 8 | 4-methylphenyl |
| 9 | 4-methyl-2-sulfophenyl |
| 10 | 2-sulfophenyl |
| 11 | 3-sulfo-4-aminophenyl |
| 12 | 2,5-disulfo-4-aminophenyl |
| 13 | 3-aminophenyl |
| 14 | 4-aminophenyl |
| 15 | 2,5-disulfophenyl |
| 16 | 4,8-disulfo-naphth-2-yl |
| 17 | 5,7-disulfo-naphth-2-yl |
| 18 | 4,6,8-trisulfo-naphth-2-yl |
| 19 | 6-sulfo-naphth-1-yl |
| 20 | 8-sulfo-naphth-1-yl |

At column 12, lines 61-65, attached information should be inserted after the table.

UNITED STATES PATENT AND TRADEMARK OFFICE
CERTIFICATE OF CORRECTION

PATENT NO. : 5,777,111
DATED : July 7, 1998
INVENTOR(S) : Schumacher, et al

It is certified that error appears in the above-identified patent and that said Letters Patent is hereby corrected as shown below:

Explanation of the NMR couplings:
s - singlet; t - triplet; q - quartet; qi - quintet; m - multiplet; dd - double doublet; dt - double triplet.

Signed and Sealed this

Fifteenth Day of December, 1998

Attest:

BRUCE LEHMAN

Attesting Officer

Commissioner of Patents and Trademarks